(12) United States Patent
Feygin

(10) Patent No.: US 6,570,158 B2
(45) Date of Patent: May 27, 2003

(54) METHOD AND APPARATUS FOR INFRARED-SPECTRUM IMAGING

(76) Inventor: Hya Feygin, 853 Hillside Ave., Mountainside, NJ (US) 07092

( * ) Notice: Subject to any disclaimer, the term of this patent is extended or adjusted under 35 U.S.C. 154(b) by 0 days.

(21) Appl. No.: 09/872,210

(22) Filed: Jun. 2, 2001

(65) Prior Publication Data

US 2002/0179834 A1 Dec. 5, 2002

(51) Int. Cl.$^7$ .......................... G01N 21/17; G01N 21/35
(52) U.S. Cl. ................ 250/332; 250/339.02; 250/461.2
(58) Field of Search ............................ 250/332, 339.02, 250/461.2, 458.1, 459.1; 436/164, 165, 172; 422/52

(56) References Cited

U.S. PATENT DOCUMENTS

| | | | |
|---|---|---|---|
| 4,777,525 A | * 10/1988 | Preston, Jr. ................. | 348/111 |
| 5,265,169 A | * 11/1993 | Ohta et al. ................... | 348/552 |
| 5,846,708 A | * 12/1998 | Hollis et al. ................. | 257/253 |
| 6,055,095 A | * 4/2000 | Bawolek ...................... | 250/332 |
| 6,083,763 A | * 7/2000 | Balch .......................... | 422/105 |
| 6,187,267 B1 | * 2/2001 | Taylor et al. ................. | 422/52 |

* cited by examiner

*Primary Examiner*—Constantine Hannaher
*Assistant Examiner*—Albert Gagliardi
(74) *Attorney, Agent, or Firm*—DeMont & Breyer, LLC

(57) ABSTRACT

An imaging system for imaging infrared-spectrum electromagnetic radiation that is emitted during cellular and molecular events. A plate upon which cellular and molecular events are to occur is placed very near to an IR detector. Typically, the plate and the detector are less than about one millimeter apart. In some embodiments, no collimating or focusing optics are present between the plate and the detector.

14 Claims, 7 Drawing Sheets

METHOD AND APPARATUS FOR INFRARED-SPECTRUM IMAGING

FIELD OF THE INVENTION

The present invention relates to an apparatus and method for imaging infrared-spectrum radiation that is emitted during cellular and molecular events, such as chemical reactions.

BACKGROUND OF THE INVENTION

In assay screening, a large number of cellular events (e.g., calcium flux, etc.), physiological events and/or molecular events (e.g., chemical reactions, etc.) are monitored and analyzed. These events, hereinafter referred to as "target events," are usually carried out in parallel in an array of deposits on specimen plates. The specimen plates are typically glass or plastic slides, or multi-well (e.g., micro-titer) plates.

Due to the large number of events taking place on the plates, time-consuming methods that directly examine each deposit (e.g., microscopic examination, etc.) are unsuitable for data acquisition. Rather, a "snap shot" of the whole plate is advantageously taken via imaging systems.

Area visible-spectrum imaging techniques, such as fluorescence imaging and luminescence imaging, can be used for data acquisition. In fluorescence imaging, when a target event occurs, a detection reagent emits light (i.e., fluoresces) when excited by an appropriate excitation source, e.g., ultraviolet light, etc. The detection reagent is chosen for its ability to interact (e.g., bind, etc.) with a target or to respond to a specific stimulus that is present only if the target event occurs. The emitted light, which provides quantitative information about the event, is captured and converted to electrical signals using, for example, a charge coupled device ("CCD"). The CCD comprises an array of thousands of sensor cells that are capable of receiving radiation from multiple wells at the same time. The signals are analyzed, via suitable software, to recover information concerning the target events.

Area fluorescent imaging devices are very complex and, hence, very expensive (c.a., $100,000 to $400,000). These imaging devices typically include an excitation light source, complicated optics, filters, a CCD, in some cases a cooler for the CCD, a control unit, software, positioners, and other elements. See, for example, the fluorescence imagers (FLIPR systems) available from Molecular Devices Corporation (www.moldev.com).

Luminescent imaging (chemi- or bio-) is similar to fluorescence imaging, except that excitation radiation is not required; the target event itself emits light. But many of the luminescent reactions have such low intensity emissions that a highly optimized imaging system, including the most sensitive form of cooled CCD camera and very efficient lenses, are required.

In addition to the high cost of these imaging devices, fluorescence imaging is complicated by the requirement of having a suitable detector reagent. While specific detector reagents have been developed for various applications, there are no universally applicable reagents. See, for example, Molecular Probes, Inc. (www.probes.com).

Consequently, a less costly and less complicated alternative to visible spectrum (i.e., fluorescence and luminescence) imaging is desirable. One possible alternative is thermal or infrared (IR) imaging.

All chemical reactions and physiological processes are accompanied by a change in energy; in other words, heat is generated or absorbed. Useful information can be obtained by monitoring/measuring such thermal changes.

Several methods are available for measuring thermal changes, including, for example, calorimetry and infrared thermography. Regarding the latter technique, published PCT application WO 99/60630 discloses a method of using infrared thermography to monitor physiological and molecular events.

According to that application, a high-resolution infrared imaging system is used to monitor heat output. FIG. 1 depicts a simplified schematic of the imaging system disclosed in WO 99/60630. Imaging system 100 comprises an infrared camera 102, including optics 104, that is spaced apart (i.e., the lens has a 6 centimeter focal length) from target 106 (e.g., a multi-well plate containing reagents, cellular or non-cellular material, a living animal, etc.). Target 106 is contained within isothermal chamber 108 that reduces temperature variations. The infrared camera monitors radiated heat production from target 106 and images are recorded by central processing unit 110 for data capture and analysis.

Infrared camera 102 advantageously provides a thermal image of the entire scene. That is, if a multi-well plate with its two-dimensional array of wells is being monitored, a thermal image of each well is preferably obtained. To do this, camera 102 must either (1) incorporate a scanning mechanism that sequentially focuses radiation from each well (or groups of wells) onto the detector or (2) use a focal plane array or "staring" array.

Infrared cameras that incorporate scanning mechanisms are quite complicated. Scanning mechanisms typically comprise multiple movable reflective surfaces, a drive system to move the reflective surfaces and several lenses to focus incoming IR radiation onto the reflective surfaces. Furthermore, infrared cameras having scanning mechanisms cannot support ratiometric or comparative analysis of target events in each well, since this requires simultaneous image acquisition across all locations on the specimen plate. A focal plane array ("FPA") 212, depicted in FIG. 2, is a monolithic microelectronic device that incorporates thousands of sensing elements 214 that continuously receive IR radiation, capturing an image of the entire scene. FPA-based infrared cameras, such as camera 302 depicted in FIG. 3, do not require a scanning system. Rather, they include a single monolithic FPA detector 212 and optics 104. Consequently, FPA-based cameras are lighter, quieter, consume less power, are more reliable, more durable and have a lower parts count than scan-based cameras. Furthermore, FPA-based cameras support ratiometric analysis. Ray tracing 318 depicts the relatively straight optical path of IR radiation from a target to detector 212 in FPA-based camera 302.

Regardless of whether the imaging system disclosed in WO 99/60630 uses a scanning system or an FPA-based camera as described above, the imaging system has certain characteristic drawbacks, which are discussed in conjunction with FIG. 4.

FIG. 4 depicts a simplified representation of the path 420 of IR radiation from target 106, through optics 104 to FPA 212. As shown in FIG. 4, the IR radiation must traverse medium 422 (e.g., air, etc.) between target 106 and optics 104, pass through optics 104 and then travel through medium 424 between optics 104 and FPA 212. The passage of IR radiation through media 422 and 424, and optics 104 attenuates the IR radiation, thereby compromising the sensitivity and resolution of the detector. Furthermore, passage of IR radiation through optics 104 introduces parallax-related aberrations.

The art would therefore benefit from infrared spectrum-imaging systems that avoid the complexity, performance deficits (e.g., reduced signal-to-noise ratio), expense and other drawbacks of prior art infrared-system imaging systems.

SUMMARY OF THE INVENTION

The present invention is an imaging apparatus and a method for imaging by which target events are monitored. Some infrared-spectrum imaging systems in accordance with the illustrative embodiment of the present invention comprise a two-dimensional detector array (hereinafter "detector"), which receives infrared radiation emitted from a specimen plate where target events are occurring. The detector is electrically connected to processing electronics that are operable to analyze the image data.

DETAILED DESCRIPTION

Figure 1:
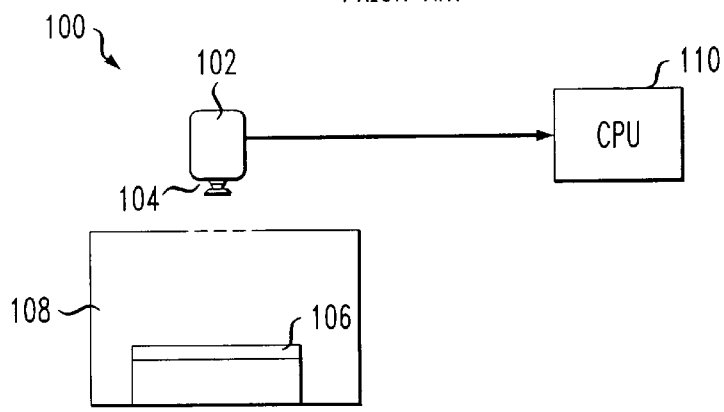
FIG. 1 depicts a simplified schematic of an imaging system disclosed in the prior art.
Figure 2:
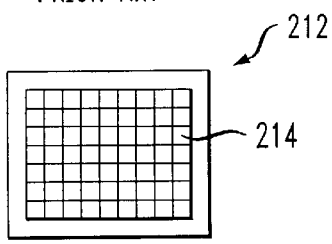
FIG. 2 depicts a conventional FPA that incorporates thousands of sensing elements for monitoring IR radiation.
Figure 3:
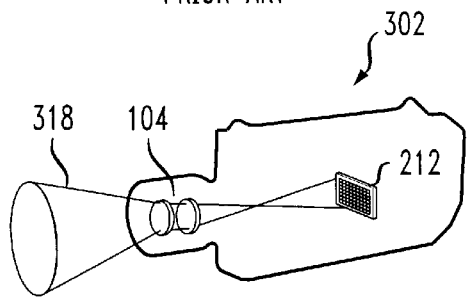
FIG. 3 depicts a prior art FPA-based infrared camera.
Figure 4:
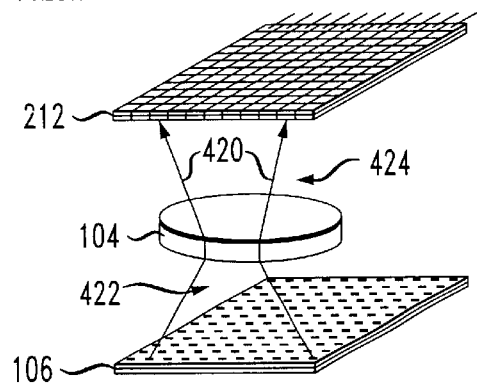
FIG. 4 depicts a simplified representation of the path of IR radiation from a target to a FPA in the prior art.

The terms listed below are given the following specific definitions for the purposes of this specification.

"Infrared Spectrum Radiation" means radiation having a wavelength within a range of about 780 nanometers to about 1 millimeter. The infrared region of the electromagnetic spectrum is sometimes broken down into three sub-regions. These sub-regions include: (1) the "near-infrared" region spanning wavelengths of about 0.7 to 1.5 microns; (2) the "intermediate-infrared" region including wavelengths of about 1.5 to 20 microns; and (3) the "far-infrared" region covering a range of wavelengths from about 20 to 1000 microns.

"Reagents" means cellular material, non-cellular material and/or chemicals. Generally, the term "reagent" means anything that is a reactant, solvent or otherwise participates in target events.

"Specimen plate" means a plate on which reagent(s) are disposed. The term "specimen plate" includes multi-well (e.g., micro-titer) plates. Such plates have a plurality of wells (96-well, 384-well, 1536-wells are typical) that are organized in a two dimensional array. The term "specimen plate" also refers to a glass or plastic slide that does not have wells, upon which reagents are deposited in large two-dimensional arrays.

"Target events" means cellular, physiological and/or molecular events, such as, for example, calcium flux, chemical reactions, etc.

"Visible spectrum radiation" means radiation having a wavelength in the visible range, which is in a range of about 390 nanometers to about 780 nanometers.

Other terms that are to be given a specific definition for the purposes of this specification are identified later herein in bold font and are set-off by quotation marks.

Imaging systems in accordance with the illustrative embodiment of the present invention incorporate known detectors that are typically operable to image infrared-spectrum radiation falling within the intermediate-infrared region.

In contrast to the prior art, some imaging systems in accordance with the illustrative embodiment of the present invention have a very small gap between the detector and the reagents on the specimen plate. Furthermore, unlike the prior art, some imaging systems in accordance with the illustrative embodiment of the present invention do not use optics (e.g., lenses, etc.) between the specimen plate and the detector.

For some imaging systems described in this specification, the space between the specimen plate and the infrared radiation detector is usually about 1 millimeter or less. The gap between the detector and the reagents on the specimen plate is less than about six millimeters, and even as small as about one millimeter. The size of this gap is a function of several parameters, including the resolution capability of the sensor as well as the geometry of the wells (for multi-well plates) and the specific arrangement of the specimen plate and the detector. A methodology for determining minimum and maximum allowable gap size is described later in this specification after several variations of an imaging system in accordance with the illustrative embodiment of the present invention are described.

Typically, each target event being monitored involves at least two reagents, one of which varies (e.g., in concentration, identity, etc.) from site to site (e.g., well to well, etc.) on the specimen plate, and the other of which does not. For example, in the study of a ligand/binding partner interaction, the binding partner is typically varied and the ligand is not. Since liquid absorbs infrared radiation, and even a small amount of liquid can compromise the operation of infrared imaging systems described herein, the amount of liquid reagent added to the specimen plates should be kept to a minimum. One way to do this is to provide the reagent that varies from site to site in a substantially solid form, such as in the form of a coating on a solid support, and merely wet the coating with the non-varying reagent. To wet the coating, the site-to-site non-varying reagent is is advantageously dispensed as an atomized or nebulized liquid.

Furthermore, for most applications, it is important that the interactions begin at the same time in each well. Consequently, the non-varied reagent should be delivered to all sites on the specimen plate at substantially the same time. This can be done by delivering the reagent as an atomized liquid. A method and apparatus for dispensing reagent as an atomized/nebulized liquid is described in "Apparatus Comprising a Reagent Atomization and Delivery System," filed on Jun. 2, 2001 as U.S. patent application Ser. No. 09/872,415 and incorporated by reference herein.

Solid support media suitable for supporting the varied reagent(s) include, without limitation, beads, pellets, disks, fibers, gels or particles such as cellulose beads, pore-glass beads, silica gels, polystyrene beads optionally cross-linked with divinylbenzene and optionally grafted with polyethylene glycol and optionally functionalized with amino, hydroxy, carboxy, or halo groups, grafted co-poly beads, poly-acrylamide beads, latex beads, dimethylacrylamide beads optionally cross-linked with N,N'-bis-acryloyl ethylene diamine, glass particles or other material having a rigid or semi-rigid surface coated with hydrophobic polymer, etc., and soluble supports such as polyethylene glycol or low molecular weight non-cross-linked polystyrene. Advantageously, 200-micron diameter PEG-grafted polystyrene beads (sold under the trademark "Tentagel™," by Rapp Polymere of Tubingen, Germany) are used as solid support media.

Although visible spectrum (i.e., fluorescence, luminescence) imaging can provide useful intensity information or other quantitative information about target events, this type of information is not reliably obtained from infrared spectrum imaging. This is because changes in emitted infrared radiation due to the occurrence of target events are quite minor in comparison with shifts in ambient temperature due to various mechanisms, including reagent evaporation, etc. Consequently, IR emissions are subject to too much background or "zero" line fluctuation noise for absolute measurements. In other words, the signal-to-noise ratio is too low.

Nevertheless, useful ratiometric (i.e., comparative) data can be obtained via infrared spectrum imaging. That is, sufficient resolution is available to use the infrared radiation emitted from two adjacent locations on a specimen plate, one of which is a control region (i.e., no reaction, etc.), to detect the occurrence of a target event. Imaging software, which assigns a color palette to relative temperature variations in the field of view with resolution of about 0.02° C., can display hundreds of hues per degree. If the color palette is referenced ratiometrically to a given control well, such that temperature fluctuations due to other physical processes (e.g., evaporation, etc.) are not considered, then all other changes (i.e., changes due to target events) are readily detectable.

Figure 5:
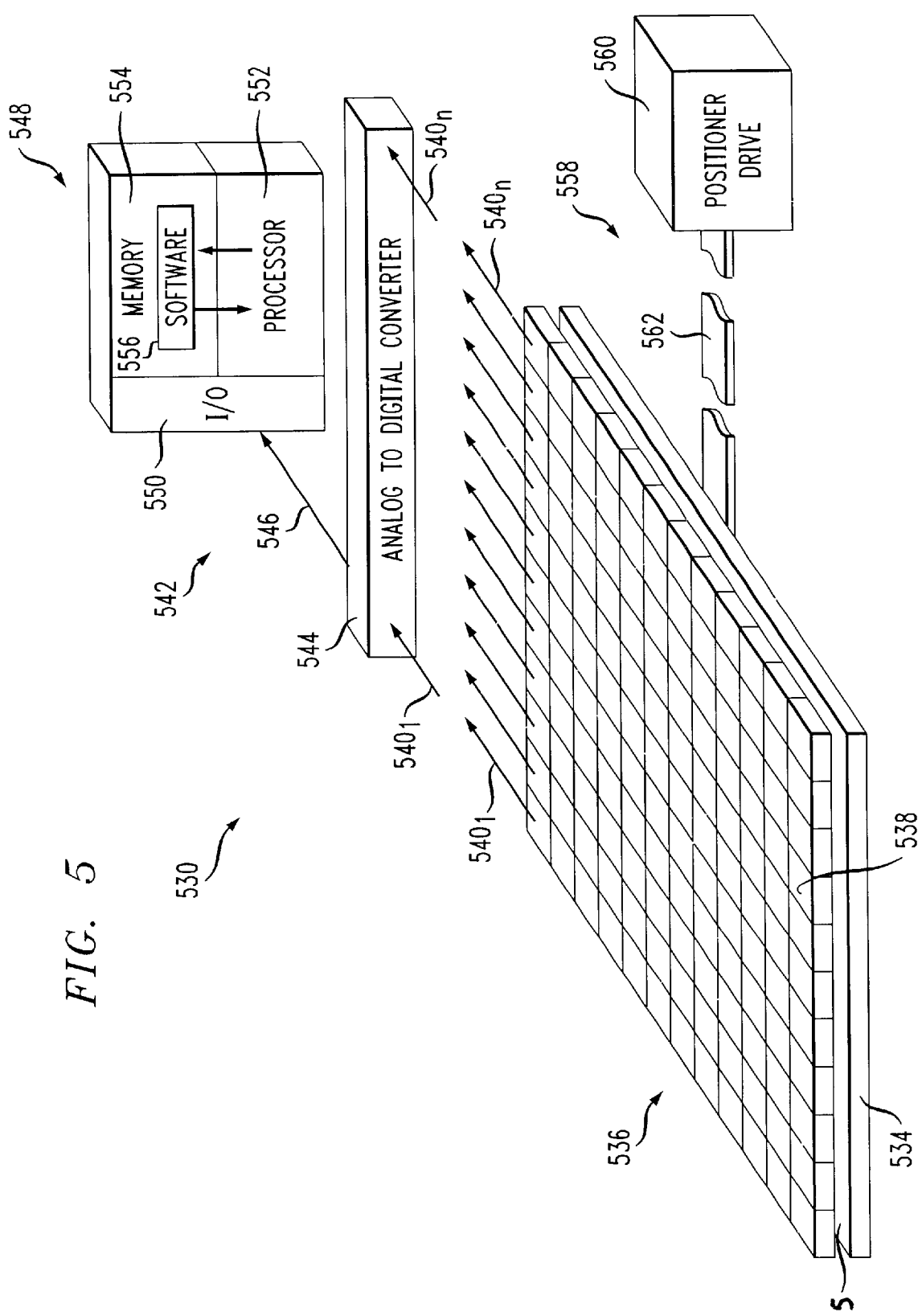
FIG. 5 depicts an imaging system in accordance with the illustrative embodiment of the present invention.

FIG. 5 depicts infrared-spectrum imaging system 530 in accordance with the illustrative embodiment of the present invention. Imaging system 530 comprises specimen plate 534, detector 536, signal processing electronics 542 and positioner 558, arranged as shown. In imaging system 530 depicted in FIG. 5, specimen plate 534 is disposed beneath detector 536. In a variation described later in this specification, specimen plate 534 is disposed above detector 536.

In one variation, specimen plate 534 is a multi-well plate, such as a micro-titer plate having, for example, 96-wells or 384-wells or 1536-wells or other formats as are known in the art. In another variation, specimen plate 534 is simply a slide or flat piece of material. And in yet a further variation, detector 536 itself serves as the specimen plate.

In use, specimen plate 534 has a plurality of reagents disposed thereon. When specimen plate 534 is a multi-well plate, reagents are contained within the wells thereof. When specimen plate 534 is a slide, reagents are advantageously disposed thereon as an array of individual deposits. When detector 536 serves as the specimen plate, the reagents are disposed on the layer of quartz or other infrared transparent material (e.g., germanium, etc.) that typically protects the sensor cells. In this specification, the term "well" is meant to include a deposit on a slide or a detector unless it is clear from the context that the description pertains only to a well.

Detector 536 detects infrared-spectrum light that is generated from target events on specimen plate 534. Infrared-spectrum light detectors incorporate materials that exhibit a response (e.g., generate an electrical signal) to some wavelengths of infrared radiation. To be suitable for use as the chemical component of an infrared detector, an infrared-responsive material must:

exhibit sufficiently high sensitivity (e.g., the ratio of electrical signal output to incident radiation power must be acceptable);

exhibit sufficiently low internal noise (i.e., due to molecular motion);

exhibit a sufficiently linear response;

respond (i.e., how quickly the detector responds to changes in the level of infrared radiation) acceptably fast; and have a sufficient bandwidth.

Illustrative materials that typically satisfy the above requirements, and that are cost effective for use, include (1) lead salts, such as PbS, PbSe and PbTe; (2) indium compounds, such as InSb, InAs and InGaAs; (3) formulations of HgCdTe; and (4) platinum silicide (PtSi).

The choice of detector material is a function of application specifics. For example, lead salts exhibit a relatively slow response speed, but offer reasonable performance without the need for cooling. For applications in which a relatively fast response is required, InSb, HgCdTe and PtSi are often a suitable choice; however, these materials must be cooled (c.a. 77K to 200K) for best performance. Such cooling decreases the internal noise of the sensor and increases the overall signal-to-noise ratio. Also, detectors can be selected based on wavelength requirements. The materials listed above all respond to near-infrared radiation and some respond to at least a portion of the intermediate infrared radiation. It is within the capabilities of those skilled in the art to select a detector material as a function of application specifics.

Detector 536, when configured to detect infrared radiation, is advantageously implemented as a two-dimensional array (often referred to as a "focal plane array" or "staring array,") well known in the art. The two-dimensional detector array comprises a regularly organized grouping of thousands of sensor elements 538. For example, a typical array might comprise 244 rows, each having 320 sensor elements, for a total of 78,080 sensor elements. Such arrays can be positioned adjacent to one another in order to create a larger detector capable of covering a larger area, such as a the size of a standard multi-well plate (i.e., 3 inches by five inches).

The radiation emitted from a particular region of plate 534 is received by only a small portion of the total of sensor elements 538 comprising detector 536. Consequently, multiple groups of sensor elements 538 are required to detect all of the target events that are occurring on plate 534. Before the detector is operated, each such group must therefore be assigned to detect the radiation being emitted from a given region (e.g., well) of plate 534, in known fashion.

When exposed to infrared-spectrum radiation having a wavelength that is within its operating range, sensor elements 538 generate an electrical response that is read-out in well known fashion. In this regard, the two-dimensional detector array is similar to the well-known CCD. Two-dimensional detector arrays are commercially available from Sensors, Inc. of Princeton, N.J., among others.

The electrical responses from sensor elements 538 are read-out and combined in known fashion to produce detector output signals $540_{i,i=1,n}$, which are delivered to signal processing electronics 542 for analysis. Signal processing electronics 542 include analog-to-digital converter 544 and data processing system 548. Analog-to-digital ("A/D") converter 544 converts analog signals $540_{i,i=1,n}$ to digital signals 546 suitable for processing by data processing system 548.

Data processing system 548 comprises input/output ("I/O") 550, processor 552, and data storage device 554. I/O 550 includes machine interfaces (e.g., input and output ports, etc.) and human interfaces (e.g., keyboard, monitor, etc.). Data storage device 554 is advantageously a non-volatile memory. Processor 552 is capable of storing data in and retrieving data from data storage device 554, and is further capable of executing programs, such as analysis software 556, that are stored in data storage device 554, and of outputting data to I/O 550. Data processing should be fast enough and powerful enough to simultaneously monitor all wells.

In some variations of the illustrative embodiment of the present invention, imaging system 530 includes positioner 558, which incorporates positioner drive 560 and drive linkage 562. Positioner 558 is used to move specimen plate 534 between a first position, wherein it is located beneath detector 536 as depicted in FIG. 5, to a second position, wherein specimen plate 534 is not beneath detector 536. This facilitates the removal and addition of reagents to specimen plate 534, for example. In a variation of imaging system 530 depicted in FIG. 5, positioner 558 can suitably engage detector 536 for movement, rather than moving specimen plate 534. Positioner 558 can be any one of a variety of mechanisms known in the art, such as, without limitation, a motorized linear positioning stage.

In accordance with the illustrative embodiment of the present invention, the source of the emitted infrared spectrum radiation (i.e., the target events) is advantageously in the immediate proximity (defined below) of the detector 536. Imaging system 530 depicted in FIG. 5 has a very small space S between specimen plate 534 and detector 536. The intent of providing space S is to keep the surface of detector 536 relatively clean. Space S is typically about 1 millimeter or less. If specimen plate 534 is a slide, rather than a multi-well plate, and the surface on which the reagents, etc., are disposed is facing sensor elements 538, then there must be a space between specimen plate 534 and detector 536. In some variations of imaging system 530 wherein specimen plate 534 is realized as a multi-well plate, the specimen plate can abut detector 536 since the level of reagents within the wells of the multi-well plate is beneath the mouth of the wells. Even though, in such a variation, there is no direct contact between detector 536 and the reagents in the wells, it is nevertheless important to clean detector 536 between successive imaging runs. This is necessary since, even without physical contact with the reagents, evaporated reagent might deposit on detector 536.

In some variations of imaging system 530, detector 536 is disposed beneath specimen plate 534. In such variations, the lower surface of specimen plate 534 can abut detector 536, regardless of whether specimen plate 534 is realized as a multi-well plate or simply a slide.

Typically, sensing elements 538 of detector 536 are covered by a thin layer of quartz or other suitable material for mechanical protection of the sensing elements. In yet a further variation of imaging system 530, reagents are disposed directly on the cover layer of detector 536, such that a separate specimen plate is not used. For such a variation, detector 536 must be cleaned between successive uses.

Regardless of the specific configuration of imaging system 530 in accordance with the illustrative embodiment of the present invention, the reagents under observation will be in the immediate proximity of detector 536.

The term "immediate proximity," as used in this specification, is defined by describing or defining a lower bound and an upper bound thereof. The lower bound is $g_{min}$, which is defined as the minimum allowable size of the gap g between reagents on specimen plate 534 and detector 536. Refer to FIGS. 6A–6F.

Figure 6A:
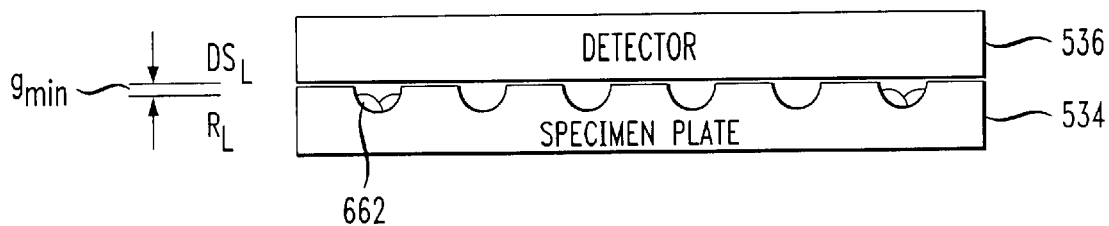
FIGS. 6A–6F depict the minimum gap between the detector and reagents for variations of the arrangement of the detector and specimen plate shown in FIG. 5.

In FIG. 6A, specimen plate 534 abuts detector 536. Minimum gap size $g_{min}$ is defined as the distance between the lower surface $DS_L$ of detector 536 and reagent level RL in wells 662. In this case, $g_{min}$ equals the distance between the reagents in wells 662 and the upper surface of specimen plate 534. The depth of a well in a 96-well plate is about 9–10 millimeters and the depth of a well in a 1536 well plate is about 1.5 millimeters. Assuming a well is at least one-half full with a reagent on a solid support (e.g., beads, etc.), $g_{min}$ for a 96-well plate is about 5 millimeters or less and $g_{min}$ for a 1536-well plate is less than 1 millimeter.

Figure 6B:
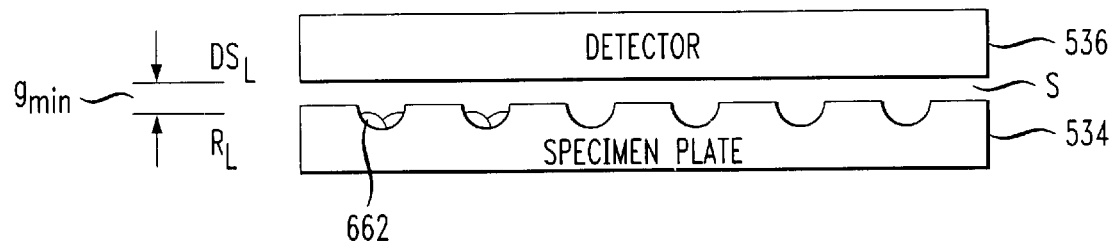

In FIG. 6B, specimen plate 534 is separated from detector 536 by space S. Minimum gap size $g_{min}$ is defined as the distance between the lower surface $DS_L$ of detector 536 and reagent level RL in wells 662. In this case, $g_{min}$ is equal to the sum of space S plus the distance between the reagents in wells 662 and the upper surface of specimen plate 534. Typically, space S is about 1 millimeter, so $g_{min}$ for a 96-well plate is about 6 millimeters or less and $g_{min}$ for a 1536-well plate is less than 2 millimeters.

Figure 6C:
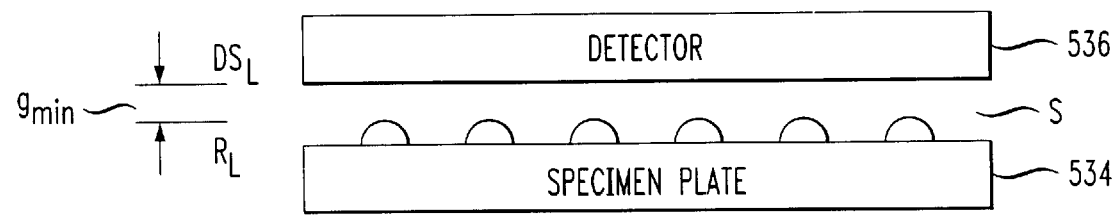

In FIG. 6C, specimen plate 534 is a slide. Reagents are disposed in an array on the upper surface of specimen plate 534. Specimen plate 534 is separated from detector 536 by space S. The space S ensures that the deposited reagents do not physically contact detector 536. Typically, the space S is about one millimeter. Minimum gap size $g_{min}$ is defined as the distance between the lower surface $DS_L$ of detector 536 and reagent level RL as measured from the top of the liquid droplet. In this case, $g_{min}$ equals the space S minus the height of the deposit above specimen plate 534. If the reagent is deposited as a liquid droplet that does not wet specimen plate 534 (i.e., the drop is substantially hemispherical), and it is assumed that the droplets are dispensed in a 1536 array, then the height of the droplet will be about 0.5 mm. Therefore, $g_{min}$ is about 0.5 millimeters.

Figure 6D:
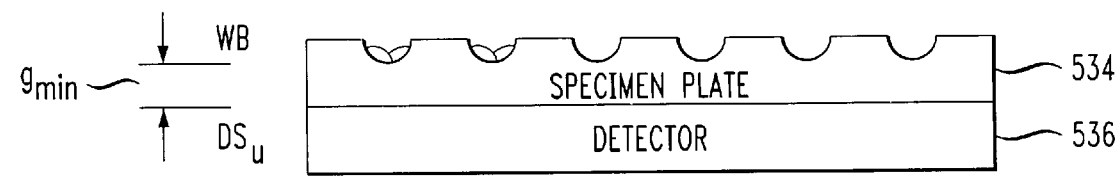

In FIG. 6D, specimen plate 534 is disposed above and abutting detector 536. Minimum gap size $g_{min}$ is defined as the distance between the bottom WB of wells 662 and the upper surface $DS_U$ of detector 536. In this case, $g_{min}$ equals the distance between the bottom WB of wells 662 and the bottom of specimen plate 534. A 96-well plate has an overall thickness of about 15 millimeters and a well in a 96-well plate has a depth of about 9–10 millimeters. Therefore, $g_{min}$ is about 5 millimeters.

Figure 6E:
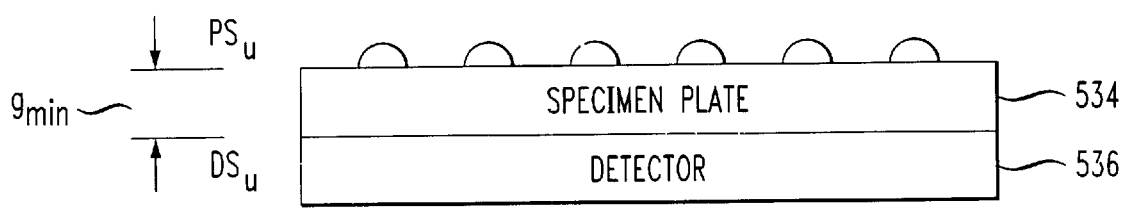

In FIG. 6E, specimen plate 534 is a slide that is disposed above and abutting detector 536. Reagents are disposed in an array on the upper surface of specimen plate 534. Minimum gap size $g_{min}$ is defined as the distance between the upper surface $PS_U$ of specimen plate 534 and the upper surface $DS_U$ of detector 536. In this case, $g_{min}$ equals the thickness of the specimen plate, which is about 1–1.5 millimeters.

Figure 6F:
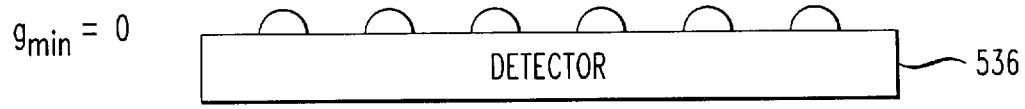

In FIG. 6F, reagents are disposed in an array of droplets directly on upper surface $DS_U$ of detector 536. In this case, $g_{min}$ equals zero.

In view of the foregoing description, it will be understood that the lower bound of the term "immediate proximity" is a function of the specific physical relationship between detector 536 and specimen plate 534. It is also be clear that, regardless of the specific variation on imaging system 530, the lower bound of the term "immediate proximity" is usually quite small, in the range of about 1–5 millimeters. Furthermore, the space S, if any, between specimen plate 534 and detector 536 is about 1 millimeter or less.

In arrangements in which the reagents are disposed on the surface of specimen plate 534 that faces the active surface of detector 536, specimen plate 534 is advantageously made from a material (such as plastics, rigid foams and the like) that does not substantially pass or otherwise conduct infrared radiation. (See FIGS. 6A, 6B, 6C.) On the other hand, for arrangements in which the reagents are disposed on the surface of specimen plate 534 that does not face the active surface of detector 536, specimen plate 534 is advantageously made from a material that is substantially transparent to infrared radiation so that emitted IR can pass through the specimen plate to reach the detector. (See FIGS. 6D, 6E.) When specimen plate 534 comprises a material that is transparent to infrared radiation, it is important to shield the system from external sources of infrared radiation.

The upper bound $g_{max}$ of the term "immediate proximity" is the maximum allowable size of the gap g between reagents on specimen plate 534 and detector 536. Refer to FIGS. 7–10.

Figure 7:
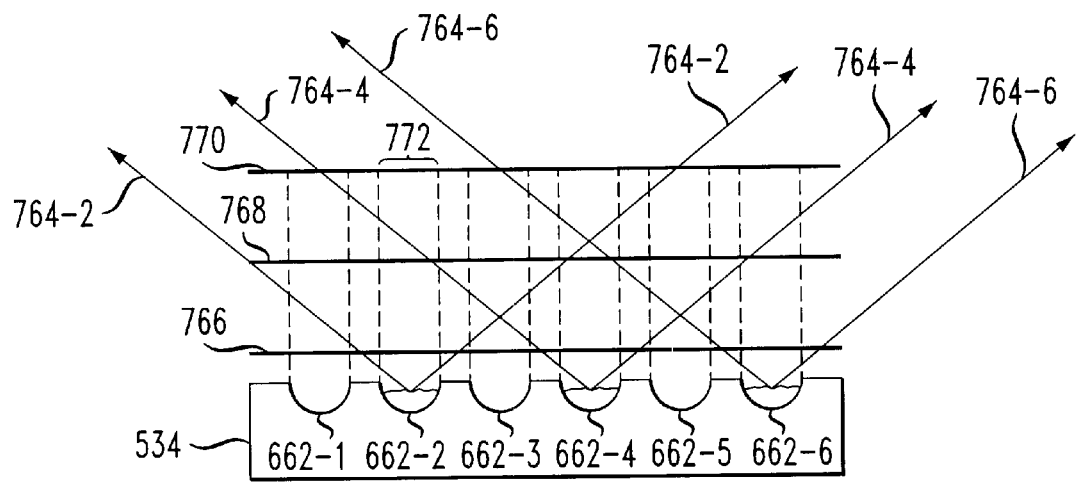
FIG. 7 depicts the divergence of infrared radiation as it radiates away from its emission site.

As gap g widens, the infrared radiation emitted from each well diverges. This phenomenon is depicted in FIG. 7. FIG. 7 depicts specimen plate 534 having a plurality of wells 662-1 through 662-6. Well 662-2 emits infrared radiation 764-2, well 662-4 emits infrared radiation 764-4 and well 662-6 emits infrared radiation 764-6. There is no emission of infrared radiation (at least due to target events) from wells 662-1, 662-3 and 662-5. Planes 766, 768 and 770 intersect the emitted infrared radiation at a successively increasing distance from the wells. For pedagogical purposes, these planes are assumed to represent the surface of detector 536 at such successively increased distance from the wells.

Dashed lines rising from the perimeter of the wells define a detection region that is associated with or assigned to each well. For example, region 772 defined within the dashed lines at the perimeter of well 662-2 is assigned to well 662-2. In this context, the term "assigned" means that infrared radiation being detected within region 772 is considered as having been emitted from well 662-2.

Figure 8:
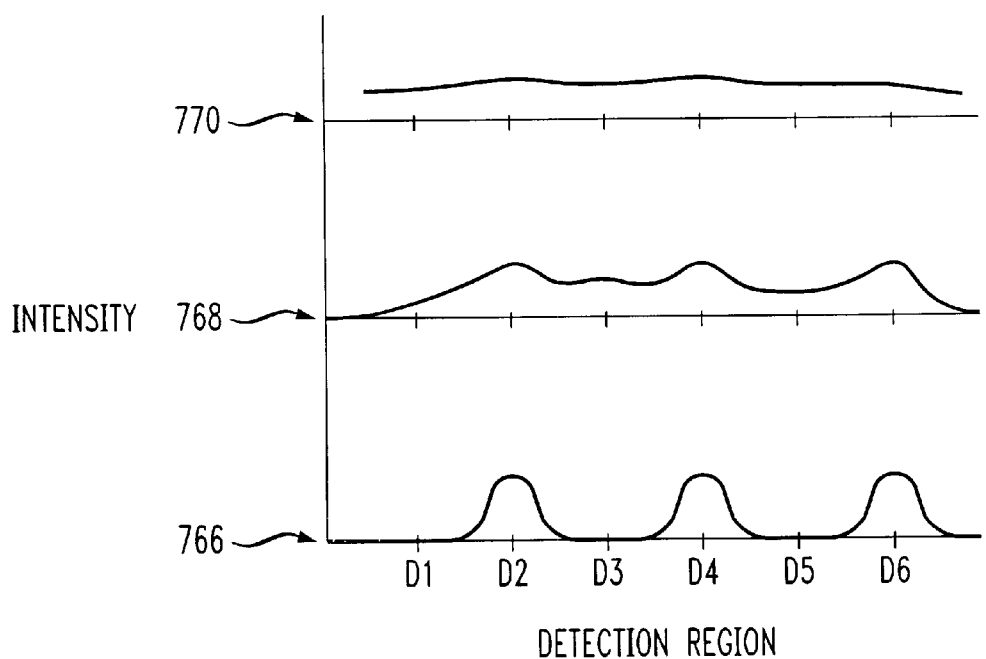
FIG. 8 depicts a plot of the intensity of infrared radiation received by a detector as a function of detection region for varying distances between the source of the emitted radiation and the detector.

FIG. 7 shows that the infrared radiation emitted from wells 662-2, 662-4 and 662-6 overlaps with increasing distance from the wells. In particular, at plane 766, no overlap is observed, and substantially all infrared radiation emitted from each well is detected at the assigned detection region and nowhere else. That is, the detection regions assigned to wells 662-1, 662-3 and 662-5 do not detect any infrared radiation (from target events). This is depicted in FIG. 8, which shows intensity as a function of detection region by way of plots for each of planes 766, 768 and 770. These plots are shown for pedagogical purposes; they are not meant to be an accurate representation of the intensity distribution corresponding to FIG. 7.

The plot of intensity for plane 766 shows that detection region D2 assigned to well 662-2, detection region D4 assigned to well 662-4 and detection region D6 assigned to well 662-6 all detect infrared radiation. On the other hand, detection regions D1, D3 and D5 assigned to respective inactive wells 662-1, 662-3 and 662-5 do not detect infrared radiation.

Referring again to FIG. 7, at plane 768, the infrared radiation that is emitted from the emitting wells overlaps or "spills over" to other wells. Consistent therewith, the plot of intensity at plane 768 (FIG. 8) indicates that infrared radiation was detected at each detection region. Although each detection region detects infrared radiation, the intensity is shown to be greatest at detection regions D2, D4 and D6. The ability to resolve such differences increases with an increase in the number of sensor elements per area on the detector (and assigned to a given well) and, of course, with the sophistication/capabilities of the associated signal processing equipment (e.g., hardware and software).

Referring again to FIG. 7, at plane 770, the infrared radiation emitted from the emitting wells now spills over to a substantial degree. The intensity plot for plane 770 in FIG. 8 is almost a flat line, indicating that the ability to resolve differences in activity between the wells has been lost. This loss in resolution is due, again, to the divergence of emitted radiation with an increase in gap g. Another problem that accompanies an increase in gap g is a reduction in signal strength that occurs as a result of the dispersion of emitted radiation due to air molecules and particles that are present in the path of the radiation.

In addition to a dependence on the number of sensing elements per area of the detector, $g_{max}$ is also dependent upon the geometry of the specimen plate. In particular, factors such as the diameter of the well, the shape of the well, and the level of the reagents in the well can each affect $g_{max}$.

A first approach to an estimate of the maximum acceptable size of $g_{max}$ of gap g is that $g_{max}$ is equal to the diameter of wells 662. According to this approach, for a 96-well plate, $g_{max}$ is about 5 to 6 millimeters, for a 384-well plate, $g_{max}$ is about 3 to 4 millimeters and for a 1536-well plate, $g_{max}$ is about 1 to 2 millimeters. Recalling the discussion of $g_{min}$, above, it is seen that, in some cases, $g_{max}$ is substantially equal to $g_{min}$.

A more rigorous procedure and arrangement for determining the maximum acceptable size $g_{max}$ of the gap g is provided below in conjunction with FIGS. 9 and 10. The procedure involves emitting infrared radiation in a discrete pattern (e.g., a "checker-board," etc.) and determining the maximum distance at which a detector can detect the pattern. For consistency with the illustrative embodiment of the present invention, $g_{max}$ is determined in the absence of lenses or other optics that would otherwise increase $g_{max}$ by virtue of focusing/collimating abilities. Therefore, when the term "immediate proximity" is used in this specification to describe a distance relationship between reagents and a detector, the use of the term is understood to preclude the presence, between the reagents and the detector, of lenses or other optics for focusing/collimating light.

Figure 9:
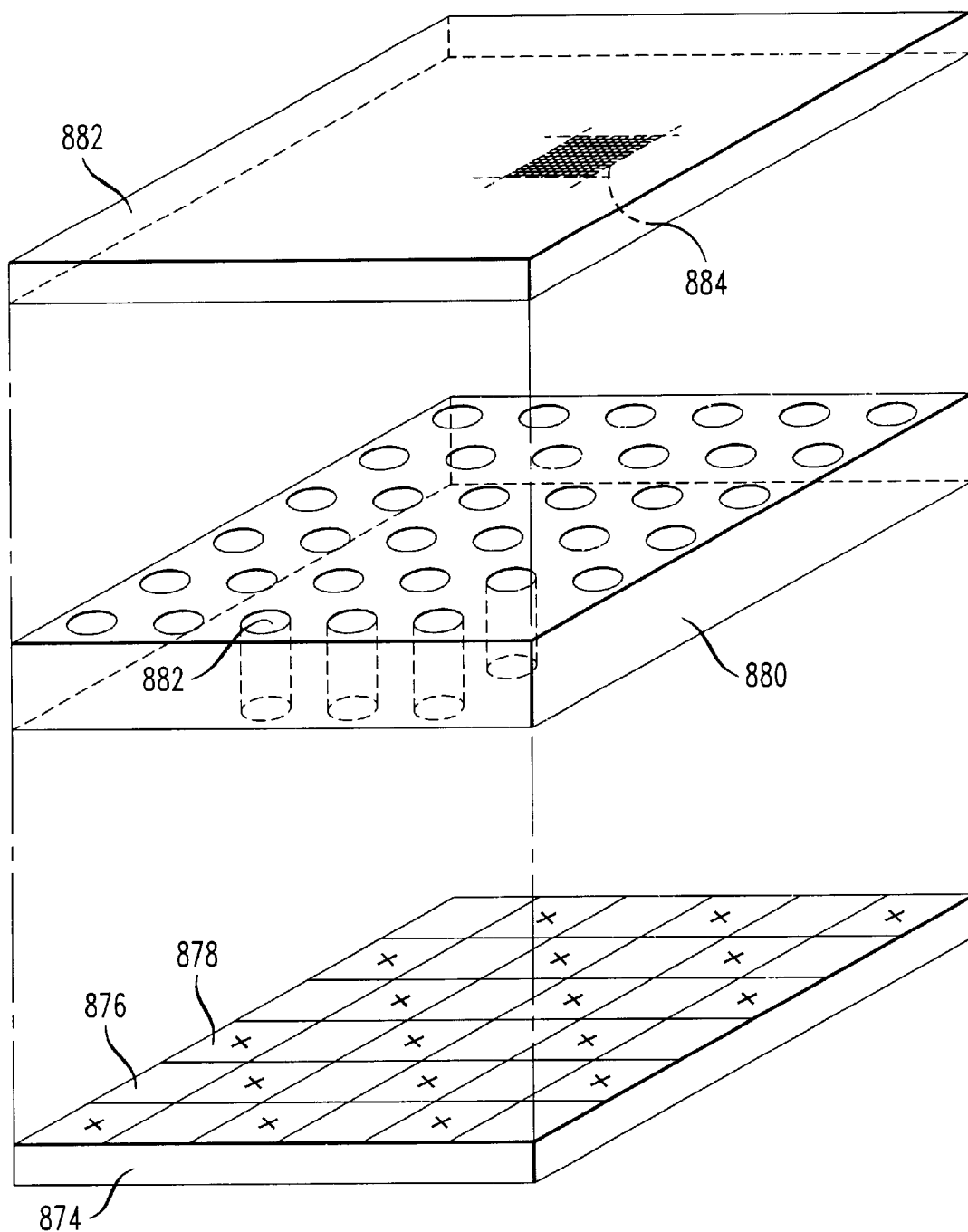
FIG. 9 depicts, via an exploded view, an arrangement for determining the maximum acceptable size of the gap between the source of emitted infrared-spectrum radiation and the detector.

FIG. 9 depicts, via an exploded view, calibrated infrared radiation source 874, well-simulating layer 880, and detector 882, arranged as shown. Other required equipment, such as processing electronics, are not depicted to keep the focus on elements that are germane to an understanding of the present invention. Calibrated infrared radiation source 874 provides, as the name implies, a source of infrared radiation. The source is calibrated such that it provides a known and consistent (e.g., three percent coefficient of variation) intensity across the surface thereof. Such calibrated radiation sources are commercially available or readily constructed by those skilled in the art. In one embodiment, calibrated infrared radiation source 874 is a metal plate comprising a metal that has high thermal conductivity (e.g., aluminum, brass, etc.) that is electrically heated by a plurality of electrical conductors.

A pattern is imposed on calibrated infrared radiation source 874 such as by placing a mask thereover. The mask comprises a thermally-insulating material, such as, without limitation, plastic or a rigid foam. Infrared radiation passes through the mask only at open regions. The configuration of open (and blocked) regions defines the pattern. For example, in FIG. 9, blocked regions 878 (which are identified by an "x") and open regions 876 are arranged in a checkerboard pattern. The pattern simulates inactive (i.e., control) wells and active wells in a multi-well plate.

As previously described, $g_{max}$ is dependent upon, among factors, the diameter of the well, the shape of the well, and the level of the reagents in the well. Since different types of multi-well plates (e.g., 96-well vs. 384 well vs. 1536-well) have different-sized diameter wells (i.e., ~5–6 mm vs. ~3–4 mm vs. ~1–2 mm, respectively), an assumption or determination should be made as to what type of multi-well plate will be used to account for these parameters. Also the level or height of the reagents in the wells during imaging should be estimated so that the distance between the mouth of the well and the reagent can be determined.

Based on this information, well-simulating layer 880 is provided. Well-simulating layer 880, which, in use, is disposed on calibrated infrared radiation source 874, includes a plurality of holes 882. Holes 882 have a diameter consistent with the wells in the multi-well plate that will be used during imaging. Well-simulating layer 880 is provided with a thickness that is equal to the distance between the mouth of the well and the top of the reagent in the well, as previously determined. The combination of calibrated infrared radiation source 874 and well-simulating layer 880 therefore mimics a multi-well plate having both inactive and active wells, and a specific height of reagent in the active wells.

Detector 882 having a plurality of sensing elements 884 is positioned above well-simulating layer 880. The detector being used for this calibration should be equivalent to the detector used in imaging system 530 (e.g., same type, same number of sensing elements per area, etc.). Groups of sensing elements 884 are assigned to each well for the purpose of data acquisition and analyses.

Figure 10:
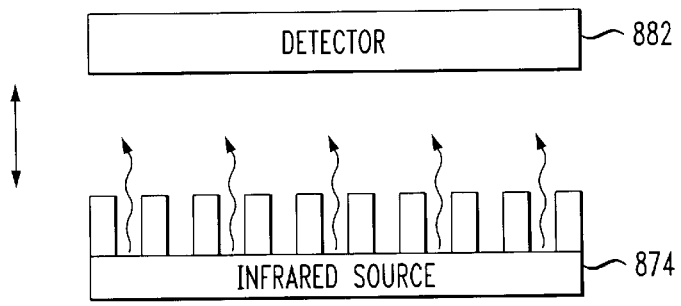
FIG. 10 depicts the arrangement of FIG. 9 in use.

Referring to FIG. 10, which depicts a simplified cross-sectional view of the arrangement shown in FIG. 9, the distance between detector 882 and the surface of well-simulating layer 880 is varied. The maximum distance at which detector 882 can resolve the simulated pattern of active and inactive wells (e.g., the checkerboard pattern, etc.) is the maximum permissible size $g_{max}$ of the gap g between reagents on specimen plate 534 and detector 536. Maximum permissible size $g_{max}$ (in the absence of a waveguide as described later in this specification) is typically less than about 10 millimeters.

Thus, the term "immediate proximity," as used in this specification, has been defined with reference to gap g between the reagents and detector 536, that falls within a range between $g_{min}$ and $g_{max}$. Gap g between the reagents and detector 536 is typically in a range between about 1 to 5 millimeters, although gap g can be zero (see FIG. 6F). And, as limited by $g_{min}$ and $g_{max}$, space S between specimen plate 534 and detector 536 is typically about 1 millimeter or less.

It might turn out that for some arrangements, and under some conditions, $g_{max}$ is less than $g_{min}$. This means that arrangement under consideration is not workable, since there will be no ability to resolve differences in activity between wells. If such a result is obtained, the geometry of the arrangement must be changed (e.g., to one of the other arrangements described herein, etc.).

In some embodiments of the present invention, imaging system 530 includes modifications that improve detection sensitivity and reduce cross talk (i.e., as caused by spill over).

Figure 11:
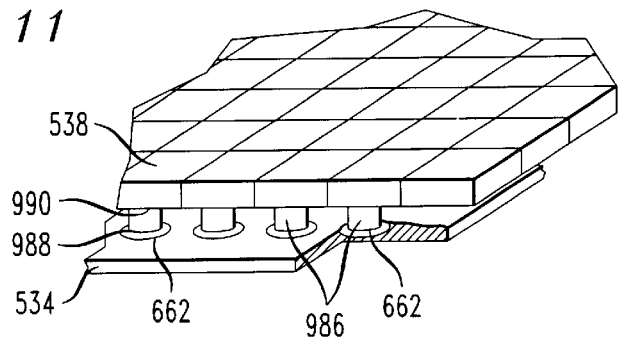
FIG. 11 depicts a variation of the imaging system shown in FIG. 5, wherein tubes are used to direct infrared-spectrum electromagnetic radiation from the wells to the detector.
Figure 12:
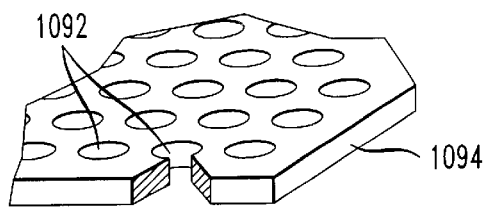
FIG. 12 depicts a further variation of the imaging system shown in FIG. 5, wherein vias are used to direct infrared-spectrum electromagnetic radiation from the wells to the detector.

Referring to FIGS. 11 and 12, a wave-guiding region directs emitted infrared radiation from wells 662 to the associated sensor elements 538. As used in this specification, the phrases "wave guide" or "wave-guiding region" refers to an element that is capable of guiding infrared-spectrum radiation along a surface by reflecting it. The phrases "wave guide" or "wave-guiding region," as used herein, exclude solid dielectric materials as are often used as optical waveguides and also excludes lenses. In a typical embodiment in accordance with the present teachings, the present waveguides include a cylindrical hollow through which the infrared-spectrum radiation passes.

For example, in one embodiment in accordance with the present teachings, each wave-guiding region is realized as tube 986, which is open at both ends 988 and 990. The inner wall (not pictured) of tube 986 is advantageously coated with an IR reflection coating, such as gold, highly polished copper, and the like. Gold plated tubes are commercially available from Epner Technologies, Brooklyn, N.Y. In various embodiments, end 988 of each tube, which is proximal to wells 662, projects partially into wells 662, or is advantageously co-planar with the mouth of the wells. Of course, the position of end 988 will depend, among other factors, upon the diameter of the tube, which in one embodiment is larger than the diameter of well 662 (so that it cannot project partially into the well).

It will be understood that sensor elements 538 have a much smaller scale than is depicted in FIG. 11; that is, the diameter of each tube 986 is much larger than a single sensor element 538.

In an embodiment depicted in FIG. 12, the wave-guiding region is realized as "through holes" or "vias" 1092 in a layer 1094 of material that is opaque at infrared wavelengths. For example, material such as thermally non-conductive plastics, rigid foams, and the like, are suitably used for this purpose. Vias 1092 are positioned in layer 1094 such that they will aligned with the matrix of wells 662 in plate 534. Layer 1094 advantageously substantially fills gap G between plate 534 and detector 536.

In embodiments in which wave guiding regions such as tubes 986 or vias 1092 are used, gap g between the reagents and detector 536 (and hence space S between plate 534 and detector 536) can be larger than in embodiments in which such wave guiding regions are not used. This is because radiation spillover should not occur and there will be far less of a decrease in radiation intensity (at the detector) as the size of gap g increases.

Figure 13:
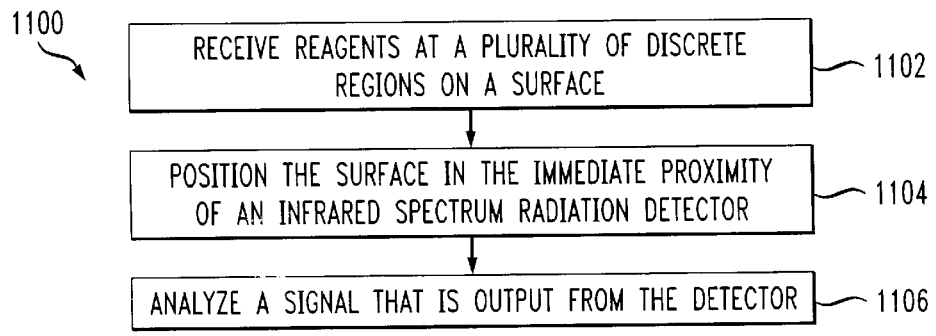
FIG. 13 depicts a flow diagram of a method in accordance with the illustrative embodiment of the present invention.

FIG. 13 depicts a method 1100 for imaging electromagnetic radiation in accordance with the present teachings. Step 1102 of method 1100 comprises receiving reagents, etc., at a plurality of discrete regions on a surface. The discrete regions are wells in the case of a multi-well plate. Alternatively, if the receiving surface is planar (e.g., a slide), then reagent is simply dispensed at discrete regions at predetermined locations, such as in a two-dimensional array of, e.g., 96, 384 or 1536 deposits.

In step 1104, the surface is positioned relative to the detectors such that the reagents and the detector are in the immediate proximity to one another. In some embodiments, the surface and the detector are spaced apart about one millimeter or less.

As previously described, target events occurring on the surface emit infrared radiation. The detector receives the emitted radiation, and generates and outputs electrical signals that are representative of the received radiation at regions across the detector. In step 1106, those signals are analyzed, such as with analysis software. The results of the analysis provide, at a minimum, an indication of whether or not the target event occurs.

It is to be understood that the above-described embodiments are merely illustrative of the invention and that many variations may be devised by those skilled in the art without departing from the scope of the invention and from the principles disclosed herein. It is therefore intended that such variations be included within the scope of the following claims and their equivalents.

I claim:

1. An article for imaging infrared-spectrum radiation emitted from reagents that are disposed in an array on a specimen plate, said article comprising a detector operable to detect said infrared-spectrum radiation and further operable to output a signal indicative of the detected infrared-spectrum electromagnetic radiation, wherein, when said article is in use:

said specimen plate is disposed beneath said detector; and said reagents are in an immediate proximity of said detector.

2. The article of claim 1 further comprising said specimen plate, said plate having a surface upon which said reagents are disposed.

3. The article of claim 2 wherein said reagents are within about 10 millimeters of said detector.

4. The article of claim 3 wherein said reagents are within about 5 millimeters of said detector.

5. The article of claim 4 wherein said reagents are within about 1 millimeter of said detector.

6. The article of claim 2 wherein said specimen plate abuts said detector.

7. The article of claim 2 wherein said specimen plate is a surface of said detector.

8. The article of claim 2 wherein said surface comprises a plurality of wells.

9. The article of claim 2 further comprising a waveguide disposed between said specimen plate and said detector, wherein said waveguide guides said infrared-spectrum radiation from said specimen plate to said detector.

10. The article of claim 1 further comprising a positioner operable to move said plate from beneath said detector.

11. The article of claim 1 further comprising a positioner operable to move said detector.

12. The article of claim 1 further comprising:

software operable to analyze said signal;

memory for storing said software; and a processor operable to run said software.

13. An article comprising:

a detector operable to detect infrared-spectrum electromagnetic radiation and to output a signal indicative of the detected electromagnetic radiation;

a space between said detector and a surface that receives reagents that are the source of said infrared-spectrum electromagnetic radiation, said surface being present when said detector is detecting said electromagnetic radiation, wherein there are no optics present in said space that collimate or focus said infrared spectrum electromagnetic radiation on said detector; and a waveguide disposed in said space, wherein said waveguide guides said infrared-spectrum electromagnetic radiation from said surface to said detector.

14. The article of claim 13 wherein said waveguide comprises a tube of cylindrical hollow, wherein a waveguiding surface thereof is coated with an IR-reflection coating.

* * * * *